(12) United States Patent
Halvorsen et al.

(10) Patent No.: US 11,752,324 B2
(45) Date of Patent: Sep. 12, 2023

(54) MONITORING OF A CARDIAC ASSIST DEVICE

(71) Applicant: OSLO UNIVERSITETSSYKEHUS HF, Oslo (NO)

(72) Inventors: Per Steinar Halvorsen, Oslo (NO); Andreas Espinoza, Hovik (NO); Erik Fosse, Oslo (NO)

(73) Assignee: CARDIACCS AS, Oslo (NO)

( * ) Notice: Subject to any disclaimer, the term of this patent is extended or adjusted under 35 U.S.C. 154(b) by 0 days.

(21) Appl. No.: 14/901,023

(22) PCT Filed: Jun. 27, 2014

(86) PCT No.: PCT/EP2014/063746
§ 371 (c)(1),
(2) Date: Dec. 27, 2015

(87) PCT Pub. No.: WO2014/207225
PCT Pub. Date: Dec. 31, 2014

(65) Prior Publication Data
US 2017/0049945 A1    Feb. 23, 2017

(30) Foreign Application Priority Data
Jun. 27, 2013 (GB) ..................................... 1311494

(51) Int. Cl.
*A61M 60/538* (2021.01)
*A61M 60/515* (2021.01)
(Continued)

(52) U.S. Cl.
CPC ........ *A61M 60/585* (2021.01); *A61M 60/178* (2021.01); *A61M 60/216* (2021.01);
(Continued)

(58) Field of Classification Search
CPC .. A61M 1/1086; A61M 1/1029; A61M 1/122; A61M 1/101; A61M 2205/18;
(Continued)

(56) References Cited

U.S. PATENT DOCUMENTS

| 4,957,504 | A | 9/1990 | Chardack |
| 6,176,822 | B1 * | 1/2001 | Nix ........................ A61M 60/82 600/17 |

(Continued)

FOREIGN PATENT DOCUMENTS

| EP | 2298375 A1 | 3/2011 |
| EP | 2460545 A1 | 6/2012 |

(Continued)

OTHER PUBLICATIONS

British Search Report for corresponding application GB1311494.7: Report dated Dec. 18, 2013.
(Continued)

*Primary Examiner* — George R Evanisko
(74) *Attorney, Agent, or Firm* — CANTOR COLBURN LLP (57) ABSTRACT

A control system for a cardiac assist device includes a sensor implantable in the body at the heart or at an implanted pump of the cardiac assist device, the sensor being for detecting motion of the pump within the body and hence being for monitoring movement of the pump, where the control system is arranged to, in use: receive signals from the sensor, the signals providing information on the movement of the pump; and to process the signals to monitor the pump speed and/or to identify pump malfunction and/or cardiac assist treatment complications.

6 Claims, 10 Drawing Sheets

(51) Int. Cl.
*A61M 60/585* (2021.01)
*A61M 60/178* (2021.01)
*A61M 60/216* (2021.01)
*A61M 60/531* (2021.01)
*A61M 60/88* (2021.01)
*A61M 60/562* (2021.01)
*A61M 60/148* (2021.01)

(52) U.S. Cl.
CPC ........ *A61M 60/515* (2021.01); *A61M 60/531* (2021.01); *A61M 60/538* (2021.01); *A61M 60/562* (2021.01); *A61M 60/88* (2021.01); *A61M 60/148* (2021.01); *A61M 2205/18* (2013.01); *A61M 2205/3334* (2013.01); *A61M 2205/3365* (2013.01); *A61M 2205/3375* (2013.01); *A61M 2205/50* (2013.01); *A61M 2205/702* (2013.01)

(58) Field of Classification Search
CPC .. A61M 2205/3365; A61M 2205/3375; A61M 2205/50; A61M 2205/702; A61M 60/515; A61M 60/816; A61M 60/538
USPC ...................................................... 600/16, 17
See application file for complete search history.

(56) References Cited

U.S. PATENT DOCUMENTS

| | | | |
|---|---|---|---|
| 7,513,864 | B2 | 4/2009 | Kantrowitz |
| 7,572,217 | B1 | 8/2009 | Koenig |
| 7,988,728 | B2 | 8/2011 | Ayre |
| 2006/0229488 | A1* | 10/2006 | Ayre ................... A61B 5/02158 600/17 |
| 2008/0183287 | A1 | 7/2008 | Ayre |
| 2014/0107399 | A1* | 4/2014 | Spence ............... A61M 60/165 600/16 |
| 2015/0174307 | A1* | 6/2015 | Eckman ................... A61B 5/72 600/17 |
| 2016/0310730 | A1* | 10/2016 | Martins ............... A61M 16/024 |

FOREIGN PATENT DOCUMENTS

| | | |
|---|---|---|
| GB | 234040 | 6/1925 |
| NL | 9001953 A | 4/1992 |
| WO | 0025853 A2 | 5/2000 |
| WO | 03061473 A1 | 7/2003 |
| WO | 2005030296 A2 | 4/2005 |
| WO | 2009027522 A1 | 3/2009 |
| WO | 2012112378 A2 | 8/2012 |
| WO | 2013003370 A2 | 1/2013 |
| WO | 2014064267 A1 | 5/2014 |

OTHER PUBLICATIONS

International Search Report for corresponding application PCT/EP2014/063746 filed Jun. 27, 2014; dated Sep. 26, 2014.

Written Opinion for corresponding application PCT/EP2014/063746 filed Jun. 27, 2014; dated Sep. 26, 2014.

Alexander Iribarne, "Incremental Cost of Right Ventricular Failure After Left Ventricular Assist Device Placement", JACC Apr. 5, 2011, vol. 57, Issue 17, Downloaded From: http://content.onlinejacc.org/ on Dec. 22, 2015.

* cited by examiner

MONITORING OF A CARDIAC ASSIST DEVICE

TECHNICAL FIELD

The current invention relates to monitoring of a cardiac assist device, such as a ventricular assist device (VAD).

BACKGROUND

Cardiac assist devices are devices used to augment or replace the blood circulatory function of a failing heart. Such devices are to be distinguished from artificial hearts, which completely replace cardiac function and are typically used when the patient's heart has been removed. Cardiac assist devices generally provide a blood pumping function to increase the flow of blood from a ventricle to the corresponding artery and hence are often known as ventricular assist devices (VADs). Some VADs are intended for short term use, for example during recovery from heart attacks or heart surgery, while other implantable devices are intended for long term use (months to years and in some cases for life), typically for patients suffering from end stage heart failure.

VADs are designed to assist either the right (RVAD) or left (LVAD) ventricle, or both at once (BiVAD). The type of VAD selected for a particular patient depends on the patient's condition, the underlying heart disease and on the pulmonary arterial resistance that determines the load on the right ventricle. LVADs are most commonly used, but when pulmonary arterial resistance is high and/or right ventricular function is reduced, then right ventricular assistance or the use of a BiVAD can be required. Long term VADs are used to provide patients with a good quality of life while they wait for a heart transplantation (known as a "bridge to transplantation") or as destination therapy for end stage heart failure.

Cardiac assist devices including VADs of various types are well known and utilize various different types of pumps and control systems. There are however common requirements to all types, being a power source, a pumping device with appropriate connections for surgical implantation at the heart and a control system. The control system in newer pumps typically controls the pump to provide a constant flow and provides the ability for the flow rate to be adjusted. The flow rate might be set by the physician or surgeon.

When using implantable cardiac devices it is necessary to monitor the effect of the treatment on an on-going basis in order to identify complications and ensure that the patient is receiving optimal treatment. For example 20-40% of the patients treated with LVAD to assist the failing left ventricle suffer from right ventricular (RV) failure after implantation of the assist device. It is difficult to predict which patients will develop this RV dysfunction, but signs of high pulmonary vascular resistance increase the likelihood of RV failure. Those who experience RV failure will stay approximately 8 days longer in the ICU than those who do not. Each patients cost approximately 90 000 US$ more if he/she needs inotropic support during the ICU stay. The need for RVAD due to RV failure increases the cost by an average of 272 000 US$. RV failure increases the risk of death in LVAD patients, 11.9% vs. 23.4% with RV failure. (Preliminary report presented at the ACC conference 2011: Iribarne A et al. Incremental cost of right ventricular failure after left ventricular assist device placement. J Am Coll Cardiol. 2011).

A problem is that one has to rely on indirect or intermittent methods for the evaluation of the effect of the treatment and the performance of the device. Cardiac performance can be evaluated by invasive blood pressures, cardiac output measurements and intermittently with echocardiography in the intensive care unit (short term management), serum-levels of cardiac function markers (pro-BNP, bilirubin, transaminases), clinical markers (ankle edema, ascites, hepatic enlargement) for long term management. These techniques all require a medical professional and the presence of the patient at a medical facility. In addition, as the patient is improving and discharged to the home, only the pump flow and pressure delivered by the cardiac assist device can presently be used for monitoring the patient on an on-going basis after discharge from the medical facility.

Non-invasive motion sensors have been suggested for use in guiding the control of a heart pump. For example, U.S. Pat. No. 7,988,728 discloses the use of non-invasive sensors to monitor heart rate (and patient movement) and to control a cardiac assist device accordingly. An accelerometer is used to measure heart rate and patient movement and these measurements are used in control of a rotary pump. However, the use of these sensors can only provide basic information relating to heart rate and physical activity. The non-invasive sensors provide no direct information on cardiac performance or the performance of the cardiac assist device and can by no means provide information on complications, such as, for example, failure of the right ventricle (occurring in 20-40% of the patients with LVAD).

Control of the timing of a cardiac assist device using implantable sensors has also been described in the prior art. U.S. Pat. No. 7,513,864 describes the use of an acoustic or mechanical sensor (e.g. accelerometer) implanted in the heart to monitor heart function, with the measurements of heart rate being used to provide timing input for a cardiac assist device. These measurements provide information on the timing of the heart. They are intended to ensure correct timing of counter-pulsation in an LVAD relative to the closure of the aortic valve.

BRIEF SUMMARY

Viewed from a first aspect, the present invention provides a control system for a cardiac assist device, the system including a sensor implantable in the body at the heart or at an implanted pump or graft of the cardiac assist device, the sensor being for detecting motion of the pump within the body and hence being for monitoring movement of the pump, and the control system being arranged to, in use: receive wired or wireless signals from the sensor, the signals providing information on the movement of the pump, which may be used to determine information about pump function, vibrations caused by the impeller and blood flow patterns through the pump; and to process the signals to monitor the pump speed and/or to identify pump malfunction and/or complications to cardiac assist treatment such as failure, suction, blood clotting/emboli, air and/or tissue embolies and changes in blood viscosity.

Sensors used in this way provide continuous and direct information on cardiac performance. By means of a control system as described above it is possible to detect and address problems with the pump of the cardiac assist device and to address them before the patient is severely affected. The prior art systems discussed above do not teach the use of implantable sensors for monitoring the performance of the pump and/or for identifying pump malfunction. The reference to the sensor position at the heart or the pump includes sensors that are on the heart or pump as well as within the heart or pump. The specific location for the sensor in the broadest form of the invention is not important provided that it is capable of detecting motion of the pump, i.e. a movement of the pump within the body, so that the pump can be monitored.

The sensors may for example take the form of accelerometers, inertia based sensors, electro-mechanical position sensors, acoustic sensor elements such as ultrasound sensors, gyroscopic sensors and so on, including combinations of sensor types. The sensors may be any type of motion sensor suitable for detecting motion of the pump within the body. Accelerometers may be used as the sensors, with the acceleration data being integrated in order to determine the position of the sensor and hence monitor movement of the pump. Motion sensors of this type, which detect a movement of the pump within the body, are to be distinguished from sensors internal to the pump that are used to detect pump rotation speed. Such sensors are not capable of detecting pump movements other than the rotation speed. The present invention concerns sensors for monitoring physical movement of the pump within the body, rather than just a sensor for detecting a rotational speed of the pump.

Cardiac assist device treatment for end stage heart failure is highly invasive and costly, and infers many complications (see the INTERMACS registry (http://www.uab.edu/medicine/intermacs/) or The HeartWare Ventricular Assist System® For the Treatment of Advanced Heart Failure Briefing Document for the Circulatory Systems Device Panel Advisory Committee, 2 Apr. 2012, PMA No. P100047 for a detailed description). Pump malfunction/failure during VAD treatment can impair circulatory support and may in worst case cause sudden death. Malfunction of the VAD system can occur for many reasons, with clotting or air in the system and malfunction of the pump the most serious complications. In the INTERMACS study six of seven pump failures occurred due to clotting and necessitated exchange of the LVAD pump. Thus, these events were potential avoidable by increasing anticoagulant therapy (INR 2-3). Malfunction of the LVAD pump due to thrombus formation could potentially be detected by the existing VAD alarm system by distinct power spikes due to impaired impeller function of the pump and increased power demand. However, in the INTERMACS study no alarm was given in four of six pump failures. The apparatus of the first aspect provides a way for alarm to be raised when there is an increased risk of pump failure and therefore provides significant advantages in patient care.

The control system may advantageously be used to detect pump failure arising from any cause. For example the pump may operate inefficiently or fail completely due to clotting, embolism, tube dislodgement, suction, acute Atrial Septal Defect (ASD) and Ventricular Septal Defect (VSD), for example. These problems will affect the motions of the "healthy" myocardium and/or the motion of the pump itself.

When a sensor at the heart is used it is preferred for the sensor to be positioned at the left ventricle for a left ventricle assist device, or at the right ventricle for a right ventricle assist device. In some preferred embodiments there is a sensor at the heart and also a sensor at the pump.

In a simple case, a failure of the pump may be identified when the sensor signal diverges by a given degree from an expected or normal range of values. Processing of the sensor signals may include analysis of the raw signals, a frequency analysis, pattern recognition analysis and/or data streaming analysis. By careful characterization of the detected motion of the pump, this analysis can identify pump parameters such as the pump rpm, vibration patterns relating to fluid flow, and/or vibrations indicative of impeller performance, for example. A failure of the pump may be indicated when the pump rpm derived from the sensor signals differs from an expected or normal pump rpm by more than a given amount. For example a pump failure may be indicated when the rpm falls outside ±5% of normal rpm. The expected or normal pump rpm may be determined based on the settings of the cardiac assist device and/or based on the power supplied to the pump. Alternatively or in addition, the presence or absence of a predetermined frequency in the frequency spectrum can be used to identify pump failure or the occurrence of complications to VAD treatment, for example by reference to frequencies known to indicate certain failure complication modes. The sensor signal and/or the results of a signal analysis thereof may be compared to historical motion sensor data to identify when a failure is occurring and to identify the type of failure/complication.

Preferably the system provides an alert to the user or operator when a potential failure/complication is identified. The system may provide a continuous indication of pump rpm as identified based on the motion sensor measurements.

In a preferred embodiment the system includes a sensor that is at the heart and is for monitoring movement of the heart, and the control system is arranged to, in use: receive signals providing information on movement of the heart, process the signals to identify heart dysfunction indicative of inadequate or excessive flow rate from the cardiac assist device; and adjust the flow rate from the cardiac assist device based on the identification of such heart dysfunction in order to optimize the performance of the cardiac assist device.

In a further aspect, the invention extends to a control system for a cardiac assist device, the system including a sensor implantable in the body at the heart or at an implanted pump of the cardiac assist device for monitoring movement of the heart and/or the pump; wherein the control system is arranged to, in use: receive signals from the sensor, the signals providing information on movement of the heart and/or pump or other part(s) of the cardiac assist device, and to carry out at least one of: processing of signals providing information on movement of the heart to identify heart dysfunction indicative of inadequate or excessive flow rate from the cardiac assist device; and to adjust the flow rate from the cardiac assist device based on the identification of such heart dysfunction in order to optimize the performance of the cardiac assist device; and/or processing of signals providing information on movement of the pump to monitor the pump speed and/or to identify pump malfunction and complications affecting pump function.

As noted above, known systems involving the control of cardiac assist devices via non-invasive sensors as in U.S. Pat. No. 7,988,728 are not capable of such measurements. The preferred system described above provides all the advantages of these non-invasive systems with the potential additional advantage of direct monitoring of movement of the heart muscle and consequent benefits in the detection of heart dysfunction. Moreover, known systems using implantable sensors for control of cardiac assist devices as in U.S. Pat. No. 7,513,864 involve merely timing input. The sensors described in U.S. Pat. No. 7,513,864 and similar systems are not utilized for the detection of heart dysfunction or pump malfunction but instead are used to match the operation of the cardiac assist device to the heart rate.

It is known to implant motion sensors at the heart for the purpose of post-operative monitoring of cardiac function. A system of this type is described in EP 1458290, in which implanted motion sensors are used to follow movements of the heart muscles following heart surgery, for example to detect ischemia.

The sensors and techniques described in EP 1458290 are similar to those required by the current invention, and in fact the teaching of EP 1458290 is useful technological background for one seeking to implement the current invention. However, like the other prior art documents referenced above the disclosure of EP 1458290 fails to suggest the use of implanted sensors in the control of a cardiac assist device. In particular EP 1458290 and similar earlier disclosures of heart monitoring with implanted sensors do not suggest monitoring for heart dysfunction indicative of sub-optimal operation of a cardiac assist device, and control of the cardiac assist device to address this. There is also no teaching of the use of the sensors to identify pump malfunction.

Consequently the currently proposed system provides advances not taught or suggested in the prior art. Various serious problems with cardiac assist devices can be addressed by this system, as discussed in more detail below.

The optimization of the performance of the cardiac assist device preferably comprises an adjustment to increase the flow rate if it is determined to be inadequate, or to decrease the flow rate if it is determined to be excessive. Optimization may also in some circumstances involve adjustment to a pulsing speed of the cardiac assist device, where it is a device with a pulsatile pumping characteristic. Adjustments to the flow rate from the cardiac assist device may occur continuously or periodically at regular intervals. It is preferred for the flow rate to be adjusted based on a closed loop control of the flow rate in response to the identification of heart dysfunction indicative of inadequate or excessive flow rate.

When the flow delivered by the pump is excessive the pump can empty the blood from the heart. This gives rise to a risk of pump failure (suction problems) with corresponding circulatory collapse. This problem may initially be detected by the sensors as a pathological increase in motion in the contracting "healthy" myocardium (reduced afterload), until a sudden decrease occurs due to suction (acute increase in afterload). Thus, in a preferred embodiment processing of the signals from the sensor to identify heart dysfunction may comprise monitoring for a progressive reduction in afterload (progressive increase in systolic motions) of the ventricle and/or monitoring for an acute increase in afterload of the ventricle (acute decrease in systolic motions), and determining that there is a potentially excessive flow rate when one or both of these occurs, with the flow rate then being adjusted downwards.

When the flow delivered by the pump is inadequate this increases the demand to the remaining contracting myocardium. This may also cause circulatory collapse. This problem can be detected by a gradual decrease in contractility (motion) in the "healthy" myocardium. Eventually it will result in the occurrence of a pathological motion of the contracting myocardium in the form of reduced systolic contraction and increased post systolic contraction. In animal models a decrease in systolic motion more than 40% indicates myocardial ischemia with a sensitivity of 94% and specificity of 92%. However, it remains to be tested whether this also applies in patients treated with VAD. Thus, in a preferred embodiment processing of the signals from the sensor to identify heart dysfunction may comprise monitoring for a progressive reduction in contractility and/or monitoring for heart motion indicating reduced systolic contraction and increased post systolic contraction, and determining that there is a potentially inadequate flow rate when one or both of these occurs, with the flow rate then being adjusted upwards.

The control system may advantageously also be used to detect pump failure from other causes. For example the pump may operate inefficiently or fail completely due to clotting, embolies (blood/air/tissue), tube dislodgement, suction and inflow/outflow problems, changes in blood viscosity (haemolysis), acute Atrial Septal Defect (ASD) and Ventricular Septal Defect (VSD), for example. These problems will affect the motions on the "healthy" myocardium. Clotting or thrombo-embolic events do change vibration/motion pattern/acoustic signals of the pump, but not necessarily without changes in pump flow or energy consumption. Clotting or tube dislodgement may cause pump failure resulting in inadequate flow detectable as above, ASD and VSD may cause suction detectable by its effect on the afterload as discussed above. ASD and VSD may also cause acute unloading or overloading, which may be detected by the control system as increased or decreased motion of the myocardium. An increase in afterload may be cause by thromboembolic occlusions of the outflow graft or kinking of the outflow graft. These events may be detected by accelerometer signal analysis, as show, for example, in the Figures.

In preferred embodiments the control system may be arranged to measure the corrective effect of changes in the flow rate of the cardiac assist device and to determine that there is a problem in addition to the underlying heart defect when corrective adjustments to the flow rate do not result in an expected improvement in heart function. For example if an increase in flow rate in response to heart dysfunction indicative of inadequate flow rate does not result in an expected improvement in heart function then the control system may determine that there is a potential clotting or tube dislodgement. Also, if a decrease in flow rate in response to heart dysfunction indicative of excessive flow rate does not result in an expected improvement in heart function then the control system may determine that there is a potential ASD or VSD. The control system may be arranged to monitor for increased or decreased motion of the myocardium indicative of acute unloading or overloading and to determine that there is a potential ASD or VSD when this occurs.

It is important for the patient and/or supervising medical authority to be made aware of such potential problems and hence preferably the control system is arranged to provide an alert when a problem of this nature is determined to be potentially present.

Typically a cardiac assist device delivers a fixed pump rate (RPM) giving an almost constant flow depending on pre- and afterload. However, patients may benefit from increased flow during physical activity and rehabilitation. A motion sensor placed at the heart or at the pump (or alternatively a separate sensor placed elsewhere on the body) can provide information about body motion and position of the patient. For example, such a sensor may function as a "step counter". In preferred embodiments the control system is arranged to process signals from the sensors to determine the level of physical activity of the patient and to adjust the flow rate of the cardiac assist device in response to changes in physical activity. Thus, the flow rate may for example be increased when the sensor movement indicates an increased level of physical activity by the patient.

Whilst just one sensor may be used, in preferred embodiments there are multiple sensors, for example sensors on the heart and on the pump. The sensors on the heart may include sensors on both of the left and the right ventricle. More than two sensors could be used, for example to also provide information about movement of the left or right atrium.

The sensor or sensors at the heart may be attached on the heart (epicardium), within the heart muscle (myocardium) or within the heart (heart chambers). Thus, the sensors on the left or right ventricle as mentioned above may be on the heart surface, within the myocardium or within the heart cavity and there may be sensors in more than one of these locations. A sensor may be attached at the apex of the heart.

The particular form of the sensors is not of great significance provided that they are susceptible to operation implanted within the body and provided that they are capable of providing signals that directly indicate heart motion or can be processed to determine heart motion. The sensors may for example take the form of accelerometers, inertia based sensors, electro-mechanical position sensors, acoustic sensor elements such as ultrasound sensors, gyroscopic sensors and so on, including combinations of sensor types.

Monitoring movement of the heart and characterization of this movement can be carried out by any suitable means. Acceleration data can be integrated to provide movement data and movement data can be derived from the differential of position data. The control system is preferably arranged to use position, motion and/or acceleration data to determine heart muscle activities and parameters such as afterload, contractility, preload, heart rate, systolic and diastolic function and so on.

The control system and/or sensors may be capable of wireless transmission of data within the body or outside the body. For example, hemodynamic data may be transferred wirelessly from this system to the hospital treating the patient.

The implantable cardiac assist device may be a LVAD, RVAD and BiVAD, used in the treatment of heart failure. The control system may be integrated as a part of the cardiac device and hence the invention extends to a cardiac assist device comprising the control system described above. Power to the sensors may be delivered by the power source for the cardiac assist device, for example a battery pack, with all leads incorporated into a single set of wiring for the cardiac assist device and extending between the parts external to the body including a controller of the cardiac assist device and the power source and the parts internal to the body including the implantable elements of the cardiac assist device, such as a pump and tubing, and the implantable sensors. In an alternative arrangement, there may be an external power source that is separate to the cardiac assist device and may be remotely located.

The systems described above can function over long time periods, providing valuable clinical information to the increasing number of patients having permanent or long-term devices. After hospital discharge such a system gives continuous information on heart rate, arrhythmias, ventricular performance and occurrence of ischemic events during daily activities. This offers promise for better diagnosis, earlier treatment of complications and improved guidance of interventions (medications) and pump settings. The system, including signal processing algorithms, may also be used in the follow up of patients, and to risk classify patients to "bridge to transplant" or to receive permanent implantable cardiac devices.

Viewed from a further aspect, the invention provides a method comprising use of the control system described above for cardiac assistance, monitoring of cardiac function and/or guidance of medical treatment in the acute phase or the follow-up phase. In some cases it may be beneficial to use the system for monitoring of cardiac function even when cardiac assistance is not continually required. In a preferred method, the control system is used to determine the need for a BiVAD by use of the signals from the sensor to identify ventricular failure.

In another aspect, the invention provides a method of controlling a cardiac assist device comprising: monitoring of a pump of the cardiac assist device by detecting motion of the pump within the body and hence measuring pump movement using implanted sensors; and, based on the measured movement of the pump, monitoring the pump speed and/or identifying pump malfunctions and/or complications to the cardiac assist treatment. The measured movement of the pump may be used to determine information about pump function, vibrations caused by the impeller and blood flow patterns through the pump, which can then be utilized when identifying malfunctions and complications.

This method provides advantages similar to those from the control system described above. The method may involve use of a control system as described above in relation to the first aspect and preferred features thereof. The implanted sensors may be at the pump and/or at the heart. When implanted sensors are at the heart it is preferred to use sensors at the left ventricle. This has been found to give measured accelerations and motions from which pump speed can easily be derived.

Viewed from a still further aspect the invention provides a method of controlling a cardiac assist device comprising: monitoring of cardiac function by measuring movement of the heart using implanted sensors; based on the measured movement of the heart, identifying heart dysfunction indicative of inadequate or excessive flow rate from the cardiac assist device; and adjusting the flow rate from the cardiac assist device based on the identification of such heart dysfunction in order to optimize the performance of the cardiac assist device.

This method provides advantages similar to those from the control system described above when used for controlling the cardiac assist device. The method may involve use of a control system as described above, optionally including the preferred features thereof.

The optimization of the performance of the cardiac assist device preferably comprises increasing the flow rate (for example by increasing pump speed) if it is determined to be inadequate, or decreasing the flow rate if it is determined to be excessive. Optimization may also in some circumstances involve adjusting a pulsing speed of the cardiac assist device, where it is a device with a pulsatile pumping characteristic. Adjustments to the flow rate from the cardiac assist device may occur continuously or periodically at regular intervals. It is preferred for the flow rate to be adjusted based on a closed loop control of the flow rate in response to the identification of heart dysfunction indicative of inadequate or excessive flow rate.

The method may comprise monitoring for a progressive reduction in afterload of the ventricle and/or monitoring for an acute increase in afterload (ventricular dilatation) of the ventricle, and determining that there is a potentially excessive flow rate when one or both of these occurs, with the flow rate then being adjusted downwards. The method may also or alternatively comprise monitoring for a progressive reduction in contractility and/or monitoring for heart motion indicating reduced systolic contraction and increased post systolic contraction, and determining that there is a potentially inadequate flow rate when one or both of these occurs, with the flow rate then being adjusted upwards. The method may also be used to identify and monitor diastolic dysfunction by measuring early and atrial inflow patterns and relations, thereby assessing the filling pattern of the heart. Different phases in the cardiac cycle may be identified and monitored by motion sensors alone or by also combining ECG signals to the motion sensor signals.

A preferred method includes monitoring the corrective effect of changes in the flow rate of the cardiac assist device and to determine that there is a problem in addition to the underlying heart defect when corrective adjustments to the flow rate do not result in an expected improvement in heart function. This may be done as described above in relation to the control system of the first aspect.

BRIEF DESCRIPTION OF THE DRAWINGS

Certain preferred embodiments of the invention will now be described by way of example only and with reference to the accompanying drawings, in which.

DETAILED DESCRIPTION

Figure 1:
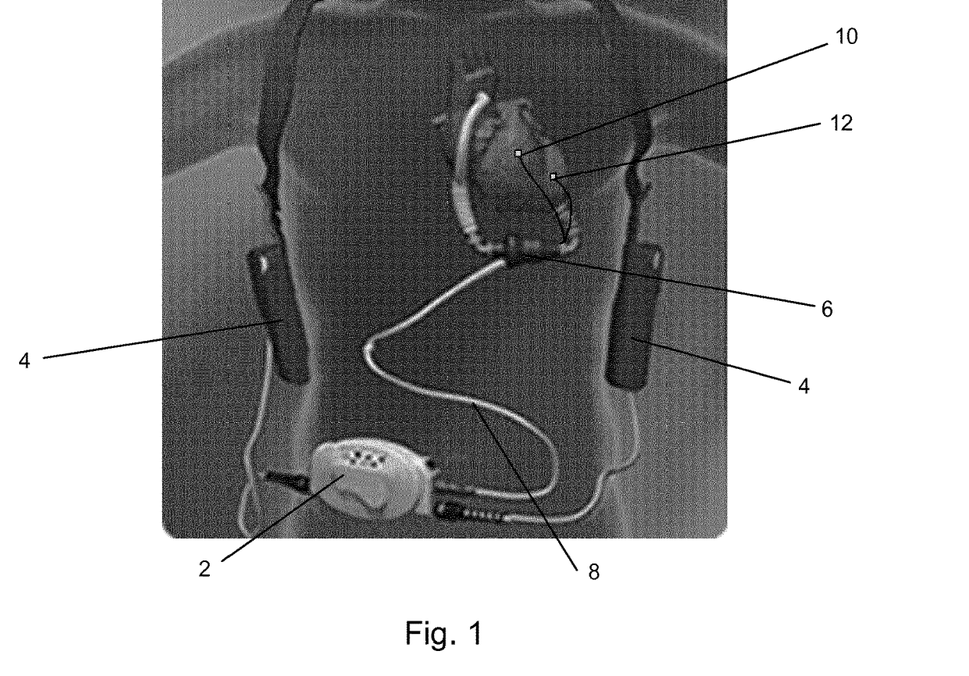
FIG. 1 shows an example of the use of implanted sensors in conjunction with a LVAD device for the human heart.
Figure 2:
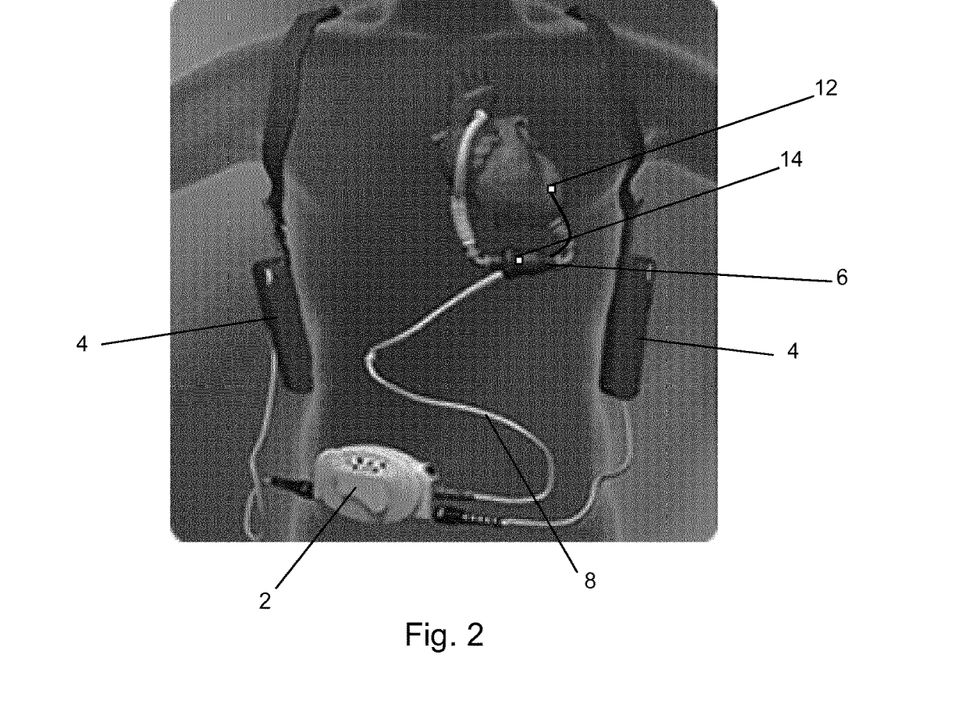
FIG. 2 shows a similar example where the implanted sensors are on the heart and at the pump of the LVAD device.

The LVAD device of FIGS. 1 and 2 is similar to conventional devices as regards its basic function in pumping blood to assist cardiac function. The LVAD comprises a controller 2, batteries 4 and a pump 6. The batteries 4 are held on the patient's body along with the controller by a harness. The controller 2 is linked to the batteries 4 by wires and control wires 8 link the controller 2 to the pump 6. The pump 6 is implanted inside the body and is connected between the left ventricle and aorta in order to provide ventricular assistance to the heart. The control wires 8 connect to the pump within the body and to the controller 2 outside of the body. They supply power and control signals from the controller 2 to the pump 6.

The example arrangement of the FIG. 1 embodiment further includes motion sensors 10, 12. A first motion sensor 10 is connected to the wall of the right ventricle, and a second motion sensor 12 is connected to the wall of the left ventricle. The control of the pump 2 by the controller 2 involves the use of data from the motion sensors 10, 12. The motion sensors 10, 12 can be any suitable sensor, such as 3-axis accelerometers, miniaturized ultrasound sensors, inertia based sensors, electromechanical position sensors and/or gyrosensors, and may for example be sensors of a type similar to those disclosed in EP 1458290.

The motion sensors 10, 12 provide signals for functional assessment of the right and left ventricle to guide therapy management (cardiac assist device settings and medical therapy). Processing of these signals is integrated into the control system of the controller 2 to thereby enable backward supervision (closed loop feedback control) to optimize the treatment of heart failure and the operation of the cardiac assist device. The control system may for example use position, motion and/or acceleration data from the sensors to determine heart movement and then monitor for changes in afterload, contractility, heart rate and other parameters of heart movement in order to identify heart dysfunction indicative of potential sub-optimal operation of the cardiac assist device. Various examples of this are set out above. The control system can also take account of other parameters including those measured at the pump such as blood pressure and so on.

The possibility to provide continuous hemodynamic monitoring (contractility and pumping capacity) and hemodynamic feedback to cardiac devices to optimize pump settings, guide the effects of medical therapy, effects of physical activity (increased demand) and to detect complications (ventricular failure, device malfunction etc.) during use of cardiac devices. Known cardiac devices do not have direct feedback systems for evaluating cardiac performance.

Motion sensor systems as described herein, for example attached to the walls of right and left ventricle, will deliver highly clinical relevant signals on myocardial contractility and ventricular performance. The sensors have been tested in various models aimed to induce both global and regional ventricular dysfunction by inducing changes in contractility (ischemia, betablocade, septic and hypotermic cardiomyopathy), preload (volume unloading and pharmacological intervention) and afterload (outflow obstruction and pharmacological intervention). The sensors are capable of detecting heart failure earlier than routine hemodynamic monitoring, and with high sensitivity. The sensors provide information about heart function very similar to echocardiography, but have an obvious advantage as continuous monitoring is possible. Signals from such sensors may also be used for guidance of treatment with implantable cardiac devices. Automated signal analysis has proved feasible with the described sensor systems and hence is implemented in the proposed control system.

The second sensor 12 in the above embodiment could be used to detect signals reflecting operation of the pump 6, in particular the speed of the pump. FIG. 2 shows an embodiment focused on monitoring of the pump 6 and it should be understood that the second sensor 12 of the embodiment above could be utilized for pump monitoring in the same way as the equivalent second sensor 12 in FIG. 2. As will be seen, the embodiment of Figure is broadly similar to that of FIG. 1 except that the first sensor 10 on the right ventricle is not present and further motion sensor, which is a pump sensor 14, is located at the pump 6.

The motion sensor 10 at the left ventricle and/or the pump sensor 14 can be used to monitor pump speed and also to detect pump malfunction as a consequence of problems such as thrombus/clotting, embolism and impeller or tube malfunction.

Pump failure is life threatening, and so is ischemic stroke due to clotting/thrombus formations and embolism. In case of thrombus formation in the LVAD it may often be necessary to change the entire pump. This is both hazardous and costly. The cost for a LVAD pump is approximately USD 120,000. However, the cost related to the operation and intensive care stay far exceeds this amount. Pump exchange is associated with a mortality of 25%. To reduce the risk of thrombus formation in the pump, the patients are anticoagulated and receive platelet inhibitors. However, too much anticoagulation infers the risk of life threatening bleedings related to both the device or to intracranial bleeding (hemorrhagic stroke). Thus, these patients are frequently monitored for level of anticoagulation (INR 2-3), hemolysis due to destruction of red blood cells by the pump, and with echocardiographic assessment of possible thrombus in left ventricle. Thus the patient frequently needs to be in contact with the hospital.

In known cardiac assist devices there is a continuous analysis of the power needed to drive the impeller within the pump. The rotation speed of the impeller is related to the pump speed (RPM) settings on the controller. If large embolis or clotting occur within the pump then energy or power needed to maintain RPM is increased. Changes in power are logged in the controller. However, studies have shown that this may not always detect device malfunction (see, for example, PMA No. P110047, and INTERMACS registry).

The cardiac assist device of FIG. 2 uses accelerometers 12, 14 to monitor the pump 6 itself. An accelerometer 12, 14 placed on the pump 6 and/or on the ventricular wall close to the pump 6 can be used to monitor complications with cardiac assist device treatment for end stage heart failure. This has been tested with three patients, where right and left ventricular function was monitored during implantation of a left ventricular assist device (LVAD). From these patients during LVAD treatment it was possible to extract information on pump mechanics, such as rotation speed (RPM) by analyzing the accelerometer signals from the accelerometer 2-4 cm from the device, which corresponds to the motion sensor 12 on the left ventricle.

Figure 3:
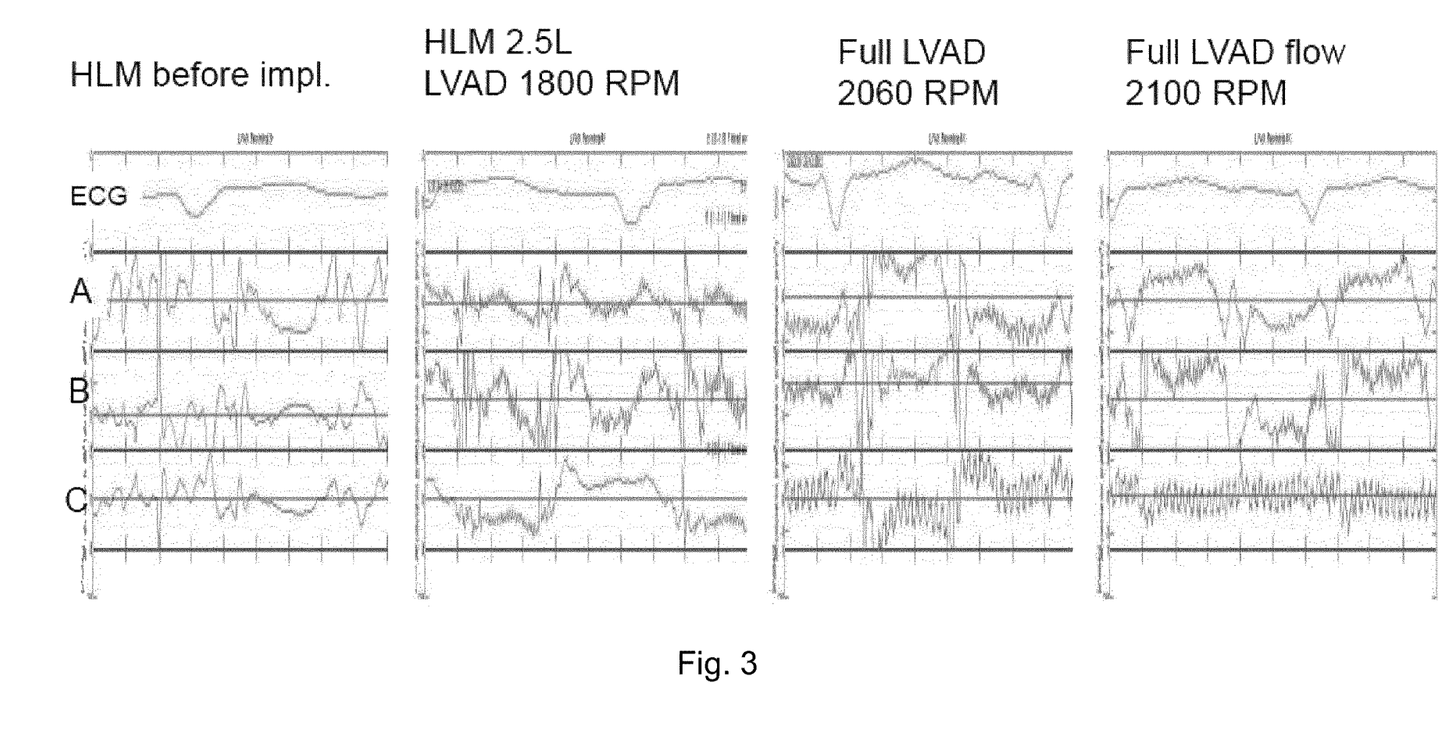
FIG. 3 is a plot of accelerometer readings obtained during LVAD treatment of a patient.

FIG. 3 shows the monitored accelerometer signals for various usages of a heart and lung machine (HLM) and LVAD. The accelerometer is a three axis device and in FIG. 3 plot A: acceleration signal in the longitudinal direction of the heart, plot B: the circumferential direction, and plot C: the radial direction. In the acceleration signals there are oscillations that correspond to LVAD RPM. The frequency distribution of the acceleration signals can be used to detect LVAD pump failure (change in higher frequencies will indicate failure).

Figure 4A:
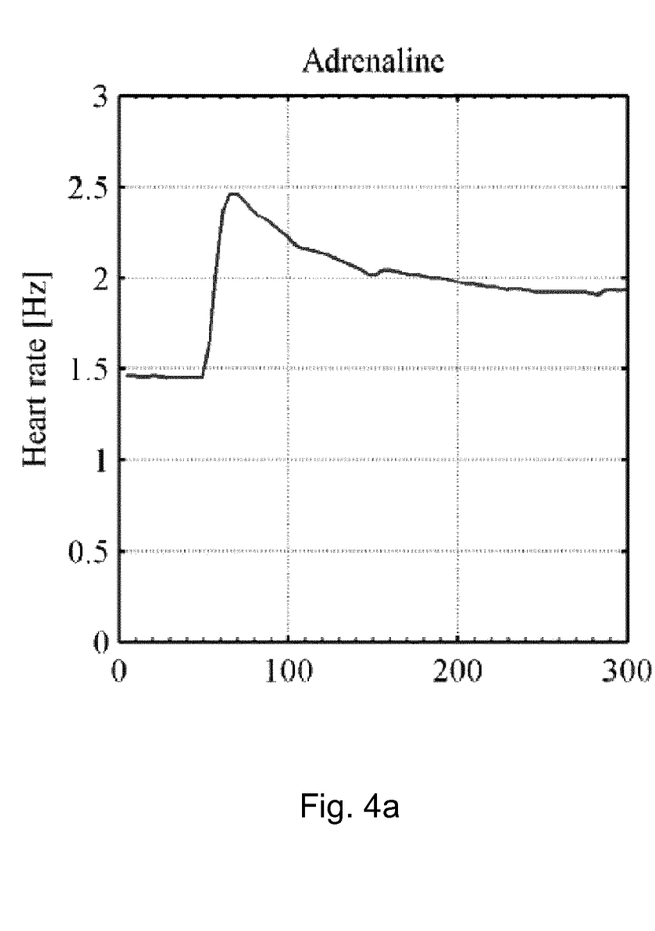
FIGS. 4a and 4b show an example of signal analysis using frequency distribution in accelerometer signals, in this case during adrenalin infusion.
Figure 4B:
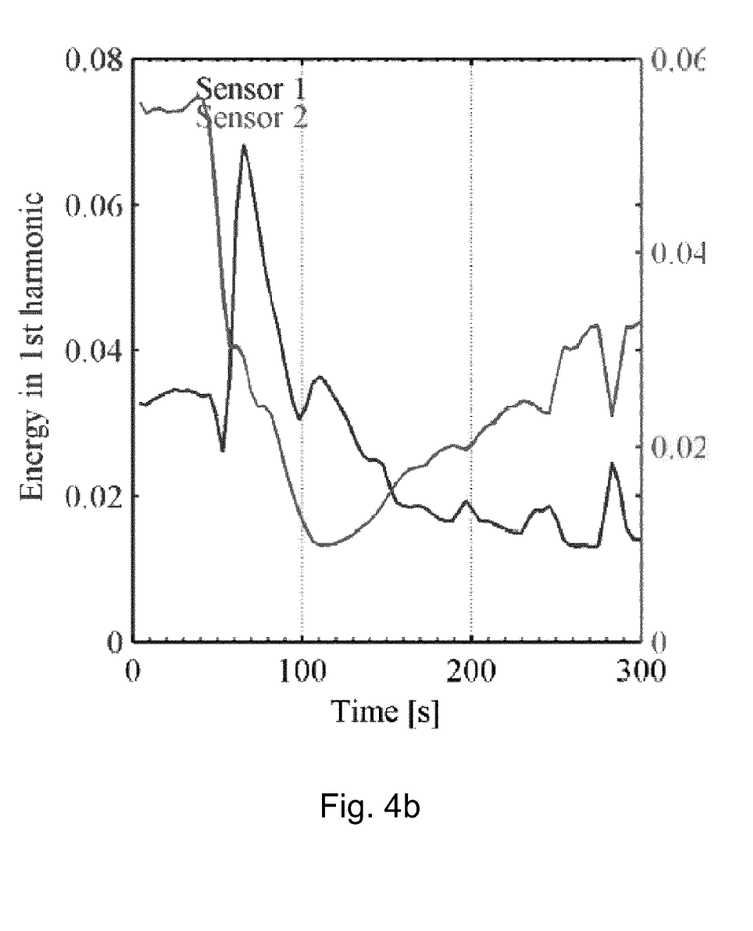

There are distinct spikes that correspond to the RPM settings on LVAD. This means that the LVAD pump caused the left ventricle to vibrate in the same frequency as the RPM settings. An accelerometer is an ideal sensor for monitoring such vibrations. From previous studies it has been shown that accelerometers can be used for monitoring heart sounds due to heart wall vibrations caused by heart valve closure. By analyzing the frequency distribution of the vibration signals it is possible to gain more information than just looking on the raw acceleration signal. This has been done to detect regional myocardial ischemia during coronary artery occlusion, but also to detect changes in global heart function (as illustrated in FIGS. 4a and 4b, which show a signal analysis for an accelerometer signal obtained during adrenaline infusion). Similarly, there will be a change in the frequency distribution of the vibration signals detected by an accelerometer placed on the ventricle if VAD malfunction/failure occurs. An accelerometer can also detect similar changes if integrated as part of the implanted VAD.

By careful analysis of accelerometer signals it is possible to determine when there is a failure or malfunction of the pump and also to determine the type of failure. This can be done, for example, by identifying certain frequencies of motion that are associated with certain failure modes and/or by comparison of the measured signals with historical accelerometer data. The historical data can include accelerometer signals for pumps without failure and also accelerometer signals for pumps that malfunctioned with a known failure mechanism. It is expected that similar types of failures will produce similar irregularities in the accelerometer signals and therefore comparison with past known failures will allow future failures to be identified.

In the above embodiments the surgical implantation of the pump 6 and the internal part of the control wires 8 can be carried out by conventional surgical techniques. The implantation of the sensors 10, 12 can be done in conventional fashion.

Figure 5:
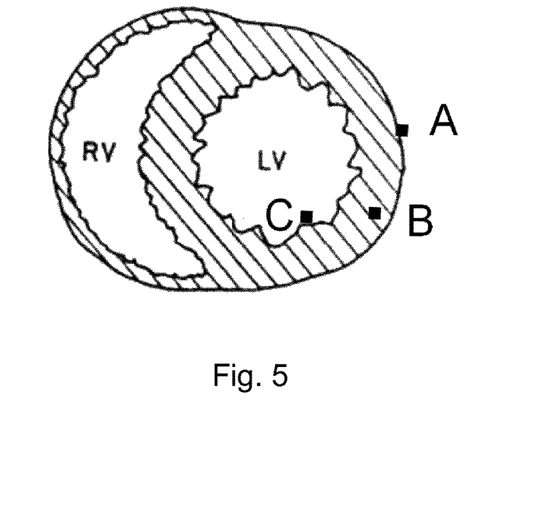
FIG. 5 is a diagram with a cross-section of the heart showing possible locations for motion sensors at the heart.
Figure 6:
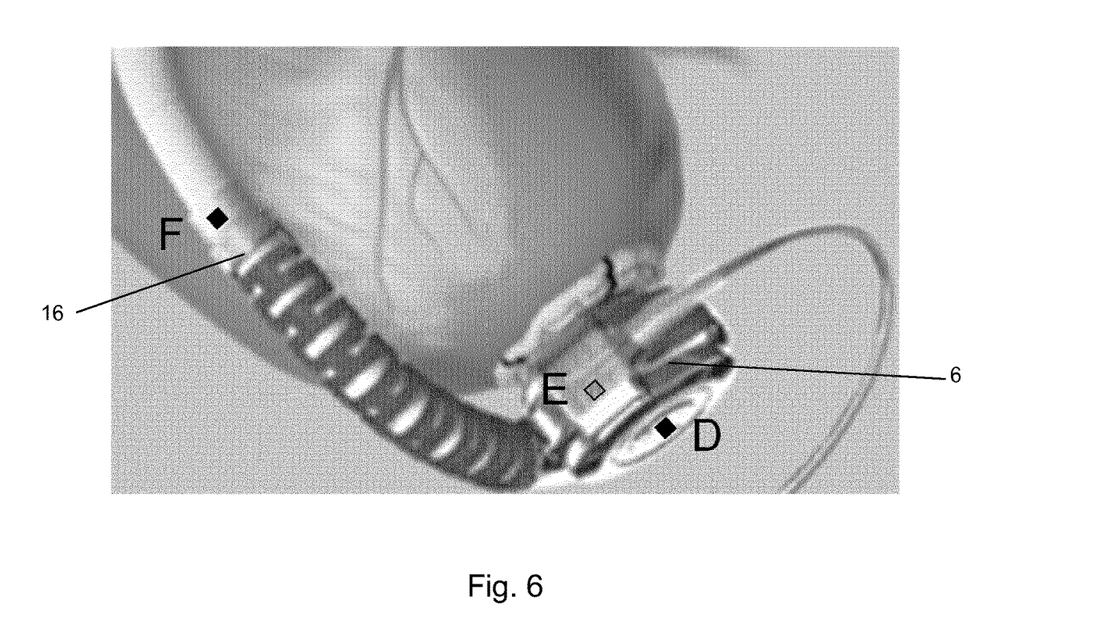
FIG. 6 shows possible locations for motion sensors at the pump and/or graft.

Possible locations for the motion sensor(s) used for the invention are shown in FIGS. 5 and 6. FIG. 5 shows a cross-section of the heart through the left ventricle (LV) and right ventricle (RV). Three general locations are shown for a motion sensor at the left ventricle, where A is an epicardial/subepicardial sensor, B is a myocardial sensor and C is an endocardial/subendocardial sensor. FIG. 6 shows a pump 6 and graft 16 and indicates three general locations for a sensor at the pump 6 or graft 16, where D is a sensor on the pump 6, E is a sensor within the pump 6 and F is a sensor on the graft 16.

It will readily be understood that although the above discussion and the Figures relate to the implanted sensors in the context of an LVAD device the sensors and control system could equally well be applied to aid the operation of an RVAD or BiVAD device, or any similar cardiac assist device for human or animal cardiac assistance and/or monitoring.

In addition, although the above example embodiments utilize two motion sensors there could alternatively be just one sensor or more than two sensors depending on the level of information required, the condition of the patient, and the cardiac assist device that is being used. For example, the system could include several of the first motion sensor 10 at the right ventricle, the second motion sensor 12 at the left ventricle, the pump sensor 14 at the pump 6 and/or a sensor at the graft 16, or just one of those sensors.

Figure 7:
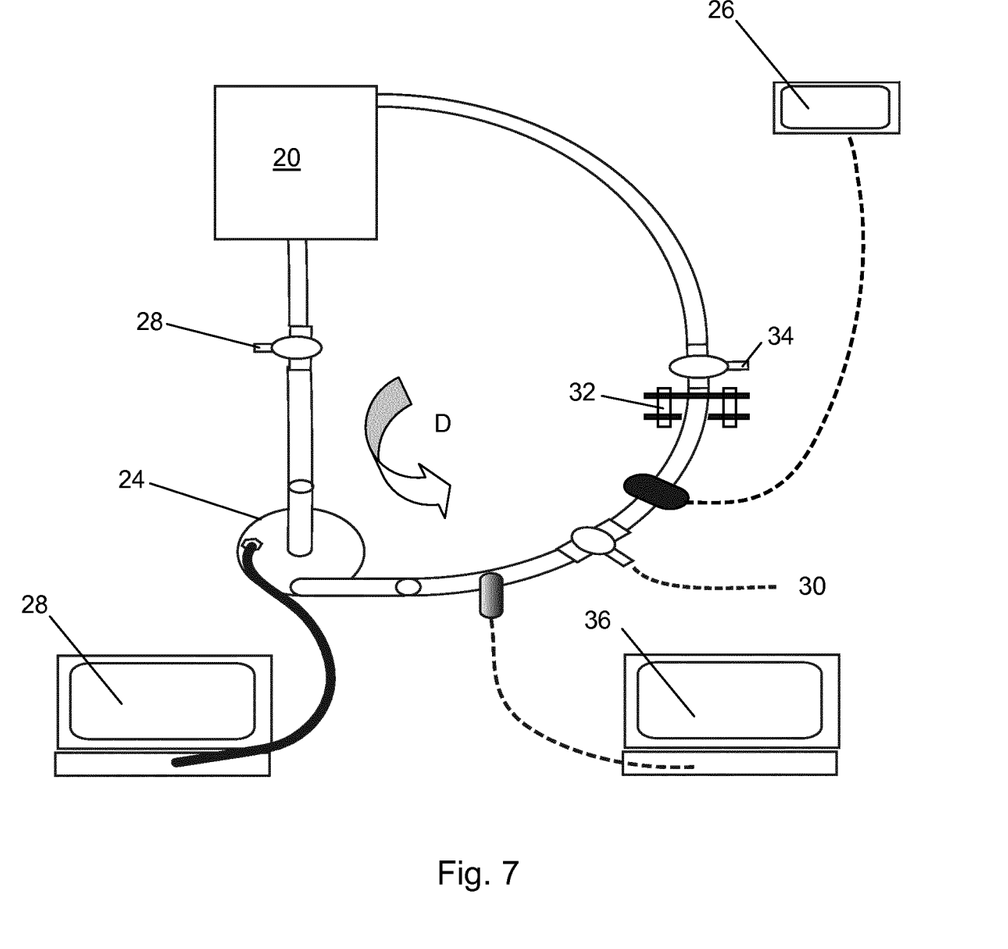
FIG. 7 illustrates an experimental set-up use for in vitro testing of the proposed sensor system with an accelerometer at a VAD in a simulated circulation system.

The proposed system has been tested in vitro and in vivo. The experimental set up used for in vitro testing of the proposed sensor system is shown in FIG. 7. This used a simulated circulatory system with flow direction as indicated by the arrow D. A reservoir 20 supplied fluid to a VAD 24 of conventional type. This was equipped with an accelerometer 28 for detecting motion of the VAD 24. The experiment used an injection port 28 for injection of thrombus/emboli into the system. A sample port 34 was also present, for sampling of the fluid. A pressure regulator 32 between the VAD and reservoir was used for preload adjustment and the preload produced by this regulator was measured using a pressure sensor 30 between the VAD 24 and the regulator 32. Also present is a spectrum analyzer 26 and Doppler sensor 36 for monitoring the circulation in the system.

Various tests were carried out to demonstrate the capabilities of the accelerometer and the results are shown in FIGS. 8 to 13.

Figure 8:
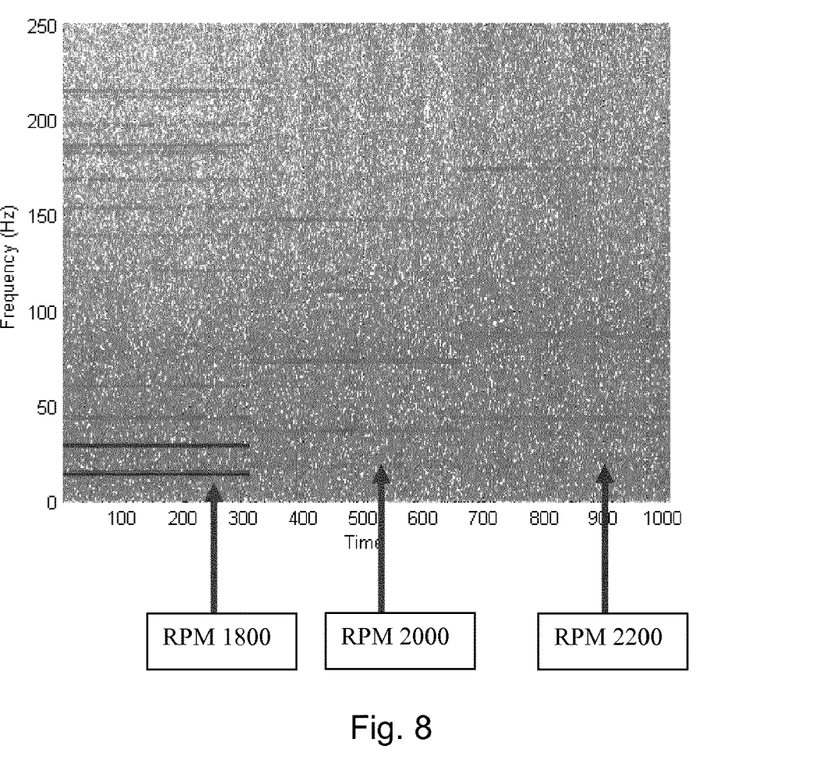
FIG. 8 is a fast Fourier transform of data from the accelerometer of FIG. 7 showing detection of VAD RPM.

FIG. 8 is a fast Fourier transform of data from the accelerometer of FIG. 7 showing detection of VAD RPM. The VAD RPM was changed between 1800, 2000 and 2200 as shown, and the accelerometer is able to easily detect this. As discussed above in relation to FIG. 3 the use of a motion sensor like an accelerometer is ideal for detecting the VAD RPM.

Figure 9:
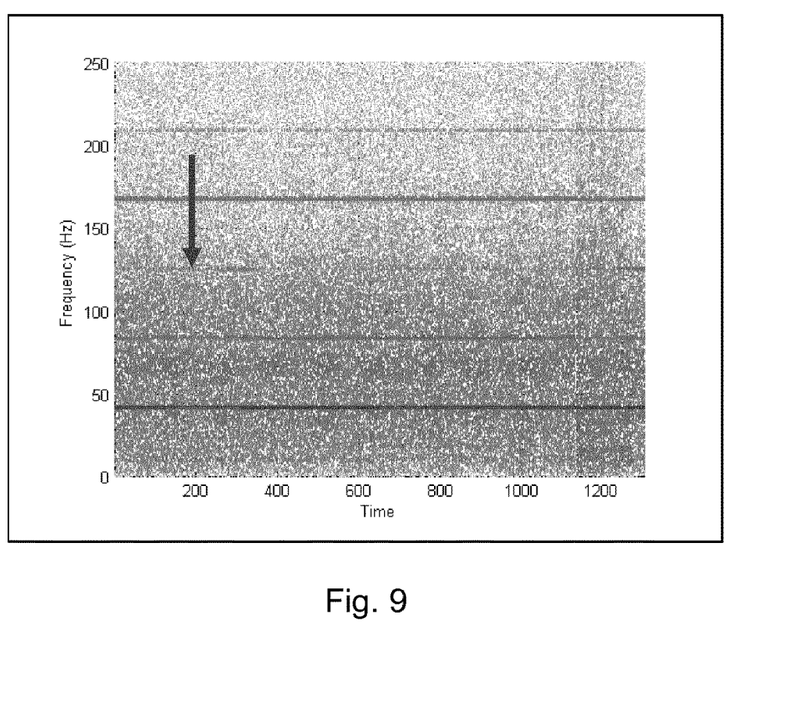
FIG. 9 is a fast Fourier transform showing detection of a simulated thromboembolism using the accelerometer.

The frequency data can also be used to detect a simulated thromboembolism as shown in FIG. 9. A third harmonic in the acceleration signal is indicative of a possible thromboembolism.

Figure 10:
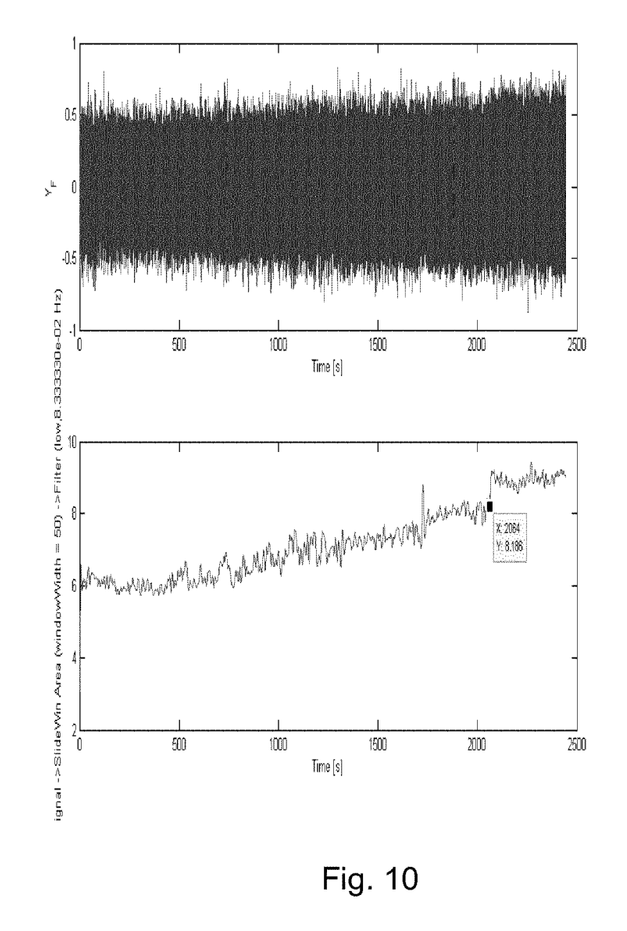
FIG. 10 illustrates changes in the acceleration signal when afterload is increased.
Figure 11:
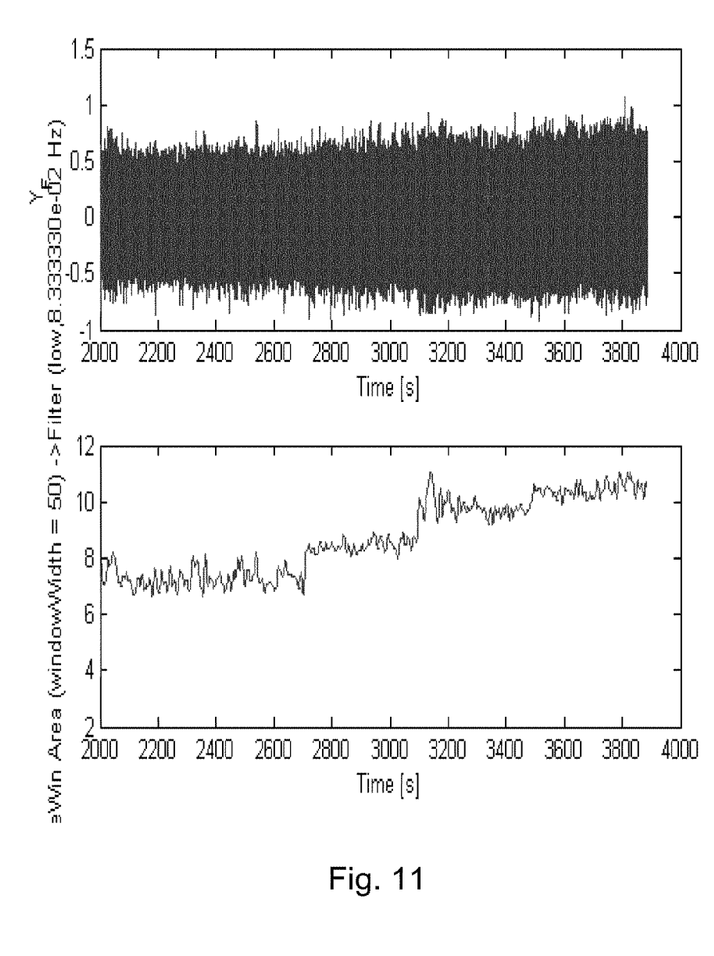
FIG. 11 shows changes in the acceleration signal when preload is decreased.

FIGS. 10 and 11 illustrates changes in the acceleration signal when the afterload or preload changes. In FIG. 10 the afterload is increased with time and this results in an increase in the amplitude of the acceleration signal. In Figure 11the preload is decreased with time and again this results in an increase in amplitude of the acceleration signal. The motion sensor can hence be used to detect changes in preload or afterload. As discussed previously this can be important in detecting potential problems.

Figure 12:
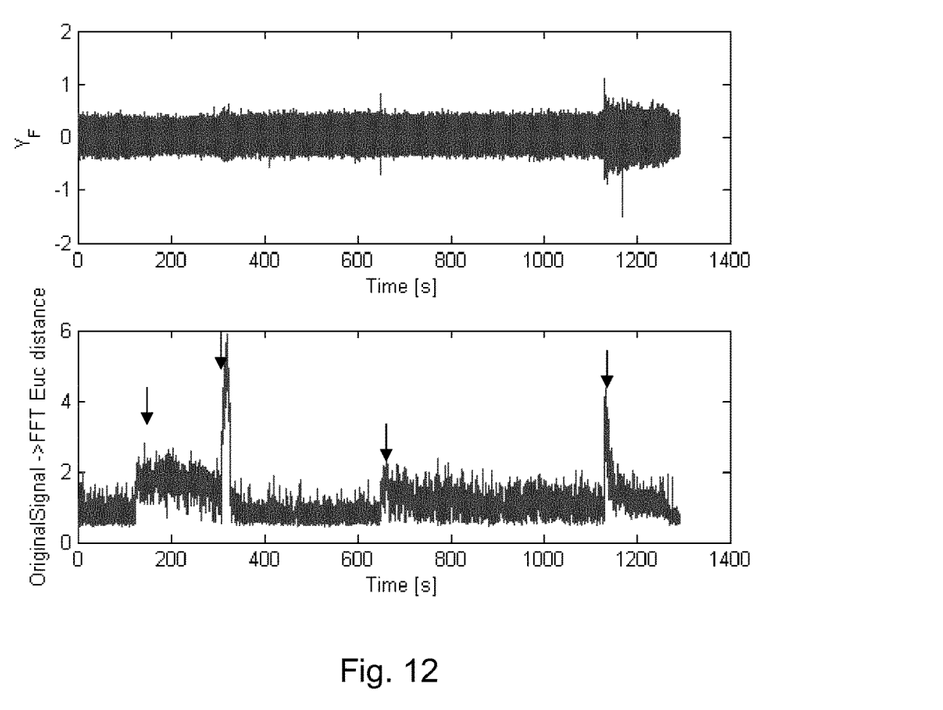
FIG. 12 shows the effects of injection of thrombus on the acceleration signal.
Figure 13:
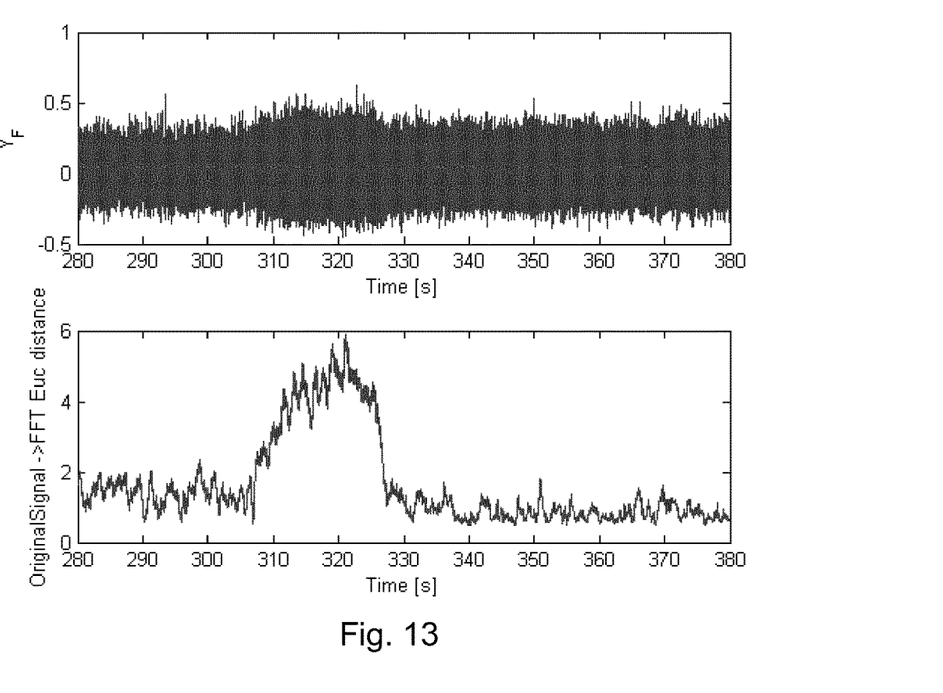
FIG. 13 is a close up view of changes during injection of a solid thrombus.

In one test various thrombi were injected into the system. FIG. 12 shows the effects of the injection of thrombus on the acceleration signal. The arrows indicate the approximate time that the thrombus was injected. From left to right, the thrombi were: 0.1 ml soft thrombus, solid thrombus, 0.25 ml soft thrombus and 0.5 ml soft thrombus. As might be expected, the larger the volume of the thrombus the greater the effect. The solid thrombus has a larger effect than the soft thrombi. FIG. 13 shows the effects of the solid thrombus in close up view.

Figure 14:
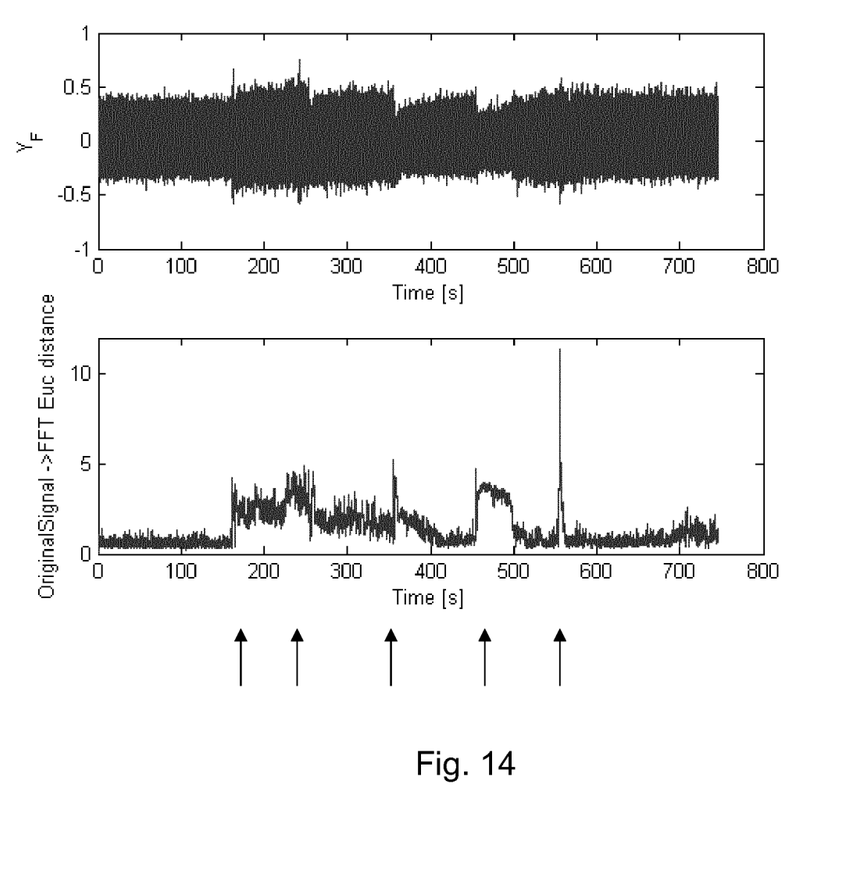
FIG. 14 is similar to FIG. 12 and shows the effects of simulated air embolisms.

Air embolisms were simulated in a similar fashion and FIG. 14 shows the effects of the simulated air embolisms on the acceleration signal. The arrows indicate the approximate timing for the injection of air. The volume of air injected, for the arrows from left to right, was 0.1 ml, 0.25 ml, 0.5 ml, 1 ml and 2 ml. It will be seen that it is possible to differentiate between air emboli, solid thrombi and soft thrombi.

Figure 15:
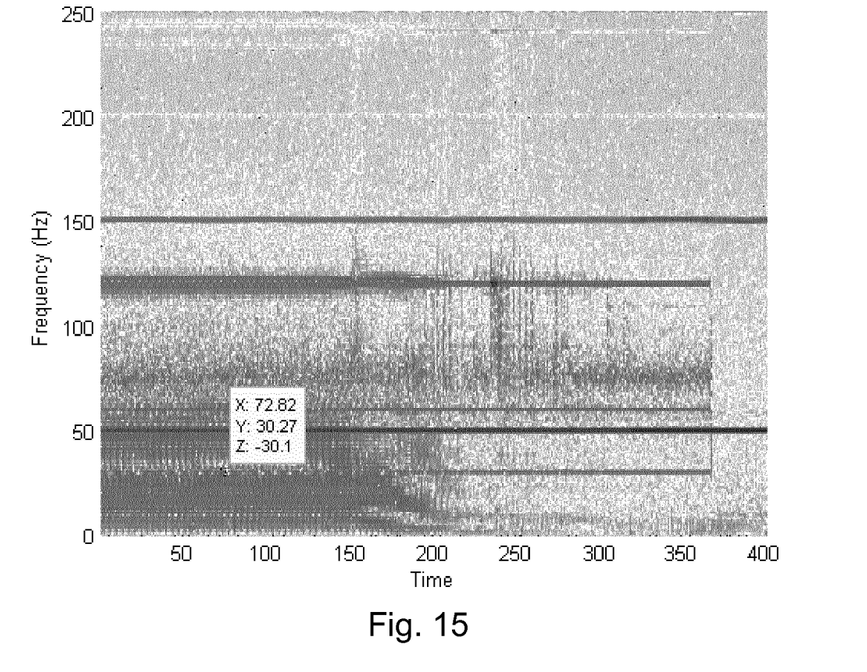
FIG. 15 is a frequency spectrum for acceleration signals from a sensor implanted in a pig for in vivo testing involving infusion of viscous material into the left ventricle and LVAD.
Figure 16:
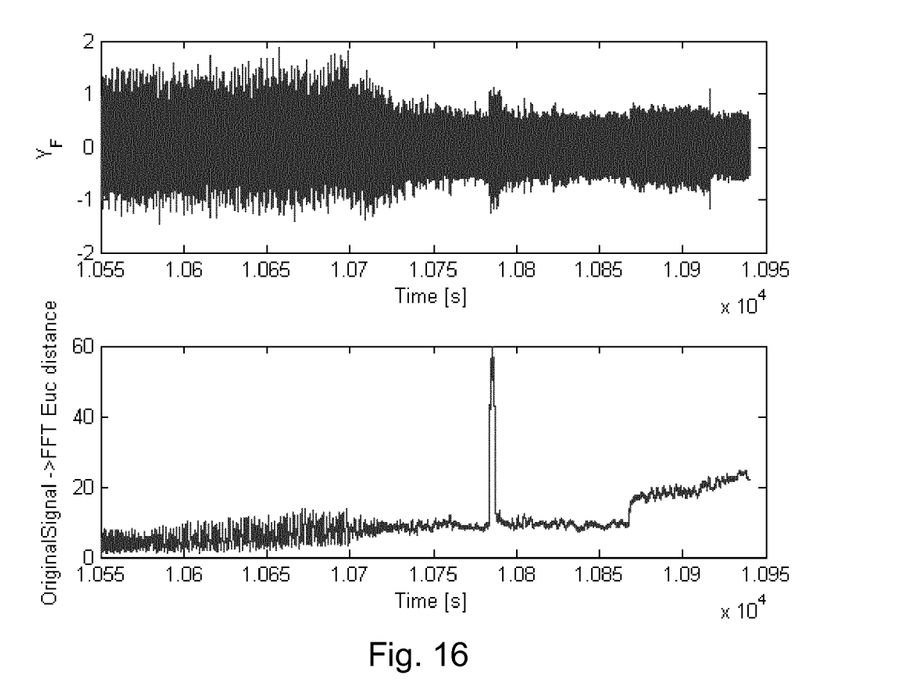
FIG. 16 shows the acceleration signals for the same in vivo testing.

The in vivo testing used a sensor implanted in a pig. The pig was equipped with a LVAD with motion sensor at the LVAD for monitoring motion of the VAD. FIGS. 15 and 16 show the data from the accelerometer when viscous material was infused into the pig's left ventricle and the LVAD. The effects of this infusion on the acceleration signal can be seen and it will be understood that they are similar to the in vitro testing.

The invention claimed is:

1. A method for cardiac assistance of a patient, the method comprising using a control system with a cardiac assist device, the cardiac assist device comprising an implanted pump and a graft, and the control system including a sensor implanted in the body at the heart or at the implanted pump or the graft of the cardiac assist device, wherein the sensor is a motion sensor, the method further including the steps of:
   detecting, with the sensor, a motion of the pump within the body and thereby monitoring the motion of the pump relative to the body;
   receiving signals by the control system from the motion sensor, the signals providing information on the motion of the pump relative to the body;
   determining information about pump function, including vibrations caused by an impeller and blood flow patterns through the pump using the signals from the sensor;
   processing the signals received from the motion sensor in order to determine an acceleration signal associated with the cardiac assist device, the processing further comprising determining a presence or absence of a third harmonic in the acceleration signal;
   providing an indication of a thromboembolism when the third harmonic in the acceleration signal is determined to be present; and
   guiding medical treatment of the patient in an acute phase or a follow-up phase based on the indication of the thromboembolism.

2. A method as claimed in claim 1, wherein the motion sensor is one of: an accelerometer, an inertia based sensor, an electro-mechanical position sensor, or an acoustic sensor element.

3. A method as claimed in claim 1, wherein the motion sensor monitors physical movement of the pump and is not used to detect pump rotation speed.

4. A method of controlling a cardiac assist device associated with a body of a patient comprising: monitoring of a pump of the cardiac assist device by detecting motion of the pump within the body and hence measuring pump movement relative to the body using an implanted motion sensor; determining an acceleration signal associated with the cardiac assist device based on the movement of the pump relative to the body as measured by the motion sensor; determining a presence or absence of a third harmonic in the acceleration signal; providing an indication of a thromboembolism when the third harmonic in the acceleration signal is determined to be present; and controlling the operation of the cardiac assist device based on the indication of the thromboembolism.

5. A method as claimed in claim 4, wherein the motion sensor is one of: an accelerometer, an inertia based sensor, an electro-mechanical position sensor, or an acoustic sensor element.

6. A method as claimed in claim 4, wherein the motion sensor monitors physical movement of the pump and is not used to detect pump rotation speed.

* * * * *